(12) United States Patent
Vedrine et al.

(10) Patent No.: US 7,182,277 B2
(45) Date of Patent: Feb. 27, 2007

(54) SPRAY DEVICE AND METHOD

(75) Inventors: Lionel Vedrine, Ridgewood, NJ (US); Laurent Barrelle, Saint Nizier du Moucherotte (FR)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 11/347,902

(22) Filed: Feb. 6, 2006

(65) Prior Publication Data

US 2006/0151629 A1 Jul. 13, 2006

(51) Int. Cl.
*A62C 11/00* (2006.01)
(52) U.S. Cl. .................. 239/329; 239/533.1; 222/129; 128/200.14; 604/239
(58) Field of Classification Search ............... 239/329, 239/533.1; 222/129; 604/89, 90, 229, 238, 604/218, 239; 128/200.14, 200.22, 207.18
See application file for complete search history.

(56) References Cited

U.S. PATENT DOCUMENTS 2,688,967 A * 9/1954 Huber ....................... 604/206
4,888,002 A * 12/1989 Braginetz et al. ........... 604/195
5,588,799 A * 12/1996 Kreitmeier .................. 604/89
5,865,799 A * 2/1999 Tanaka et al. ............... 604/89
5,944,698 A * 8/1999 Fischer et al. .............. 604/236

* cited by examiner

*Primary Examiner*—Dinh Q. Nguyen
(74) *Attorney, Agent, or Firm*—David M. Fortunato; Cohen Pontani Lieberman and Pavane

(57) ABSTRACT

A spray device including a barrel having a bypass and at least two spaced stoppers defining a first and second chambers and a spray nozzle. Movement of the first stopper drives the second stopper to the bypass and the fluid in the first chamber into the second chamber, mixing the fluid and substance. Continued movement of the first and second stoppers drives the mixture through the spray nozzle. The spray device may include a third stopper having a body in the tubular barrel which is moved toward the spray nozzle. The movement of the third stopper provides space for the mixture and prevents unpressurized fluid from flowing through the spray nozzle. The third stopper includes an axial stalk. The stalk may be deformable or the stalk may be separate from the body and the spray nozzle includes a longitudinal internal passage which provides communication with the spray port.

7 Claims, 5 Drawing Sheets

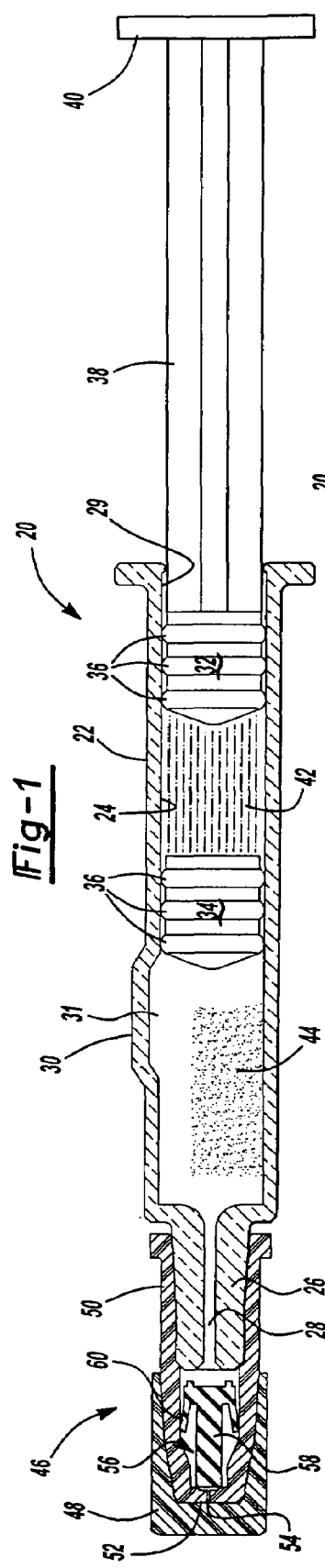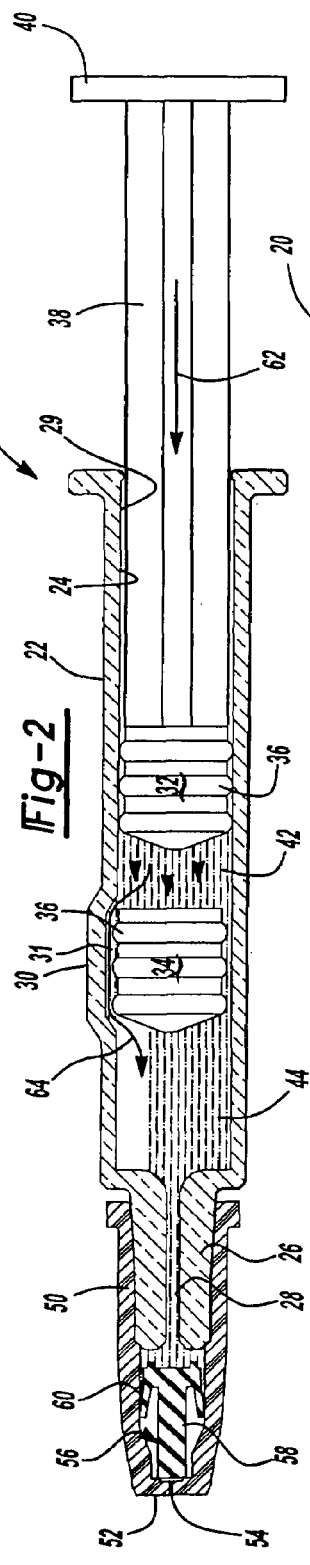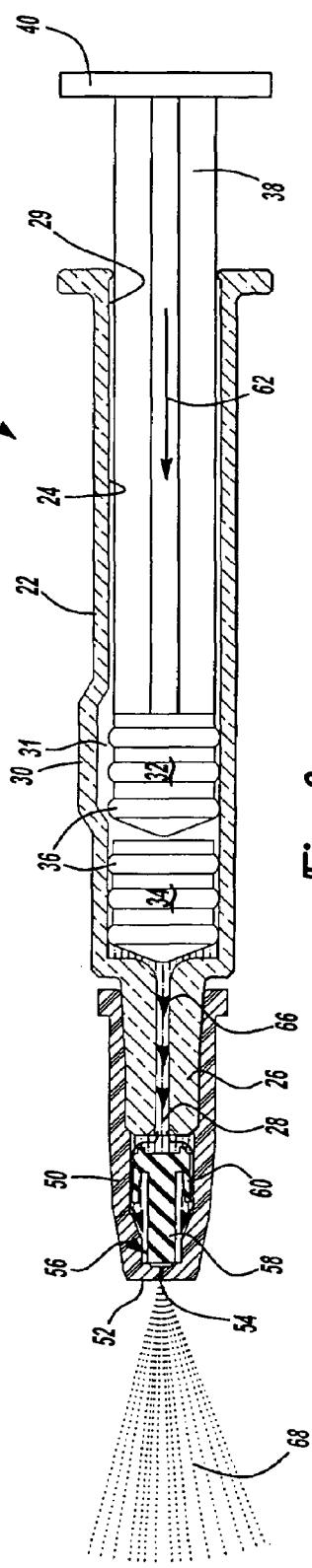

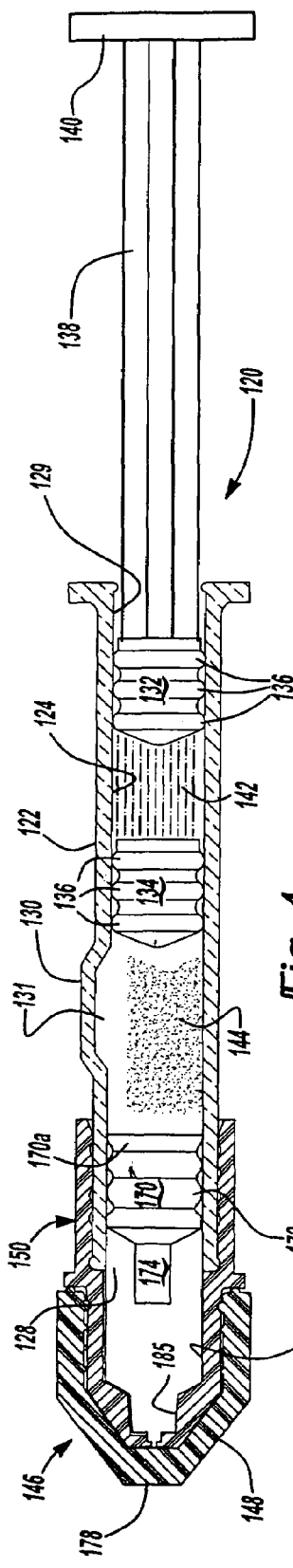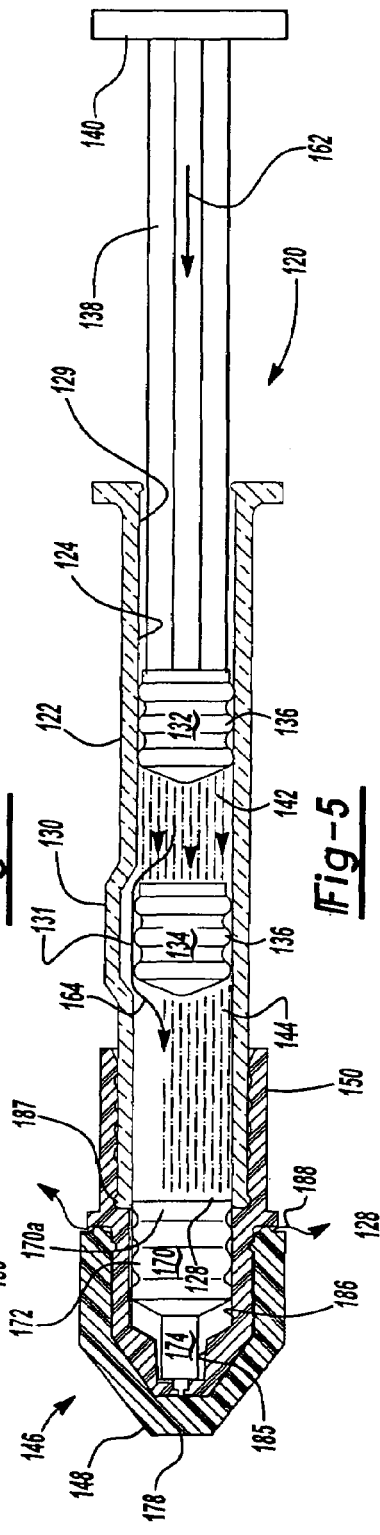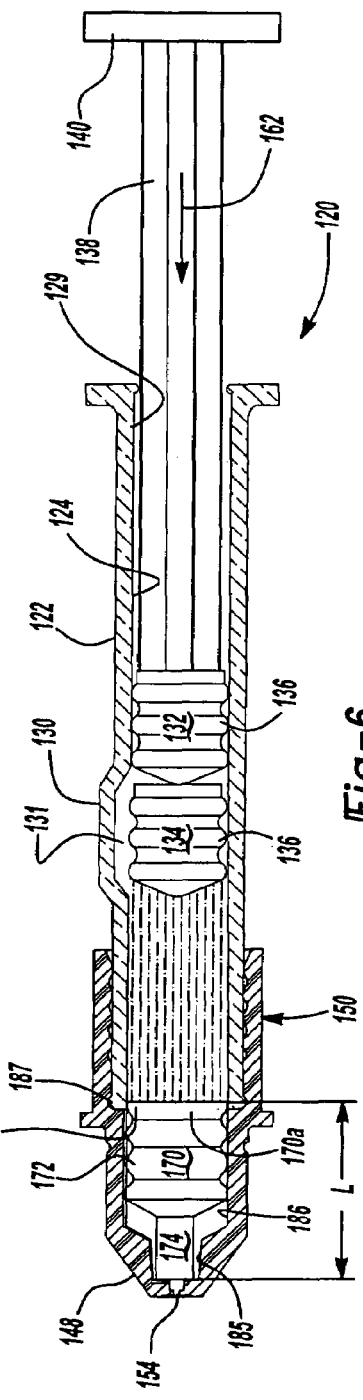

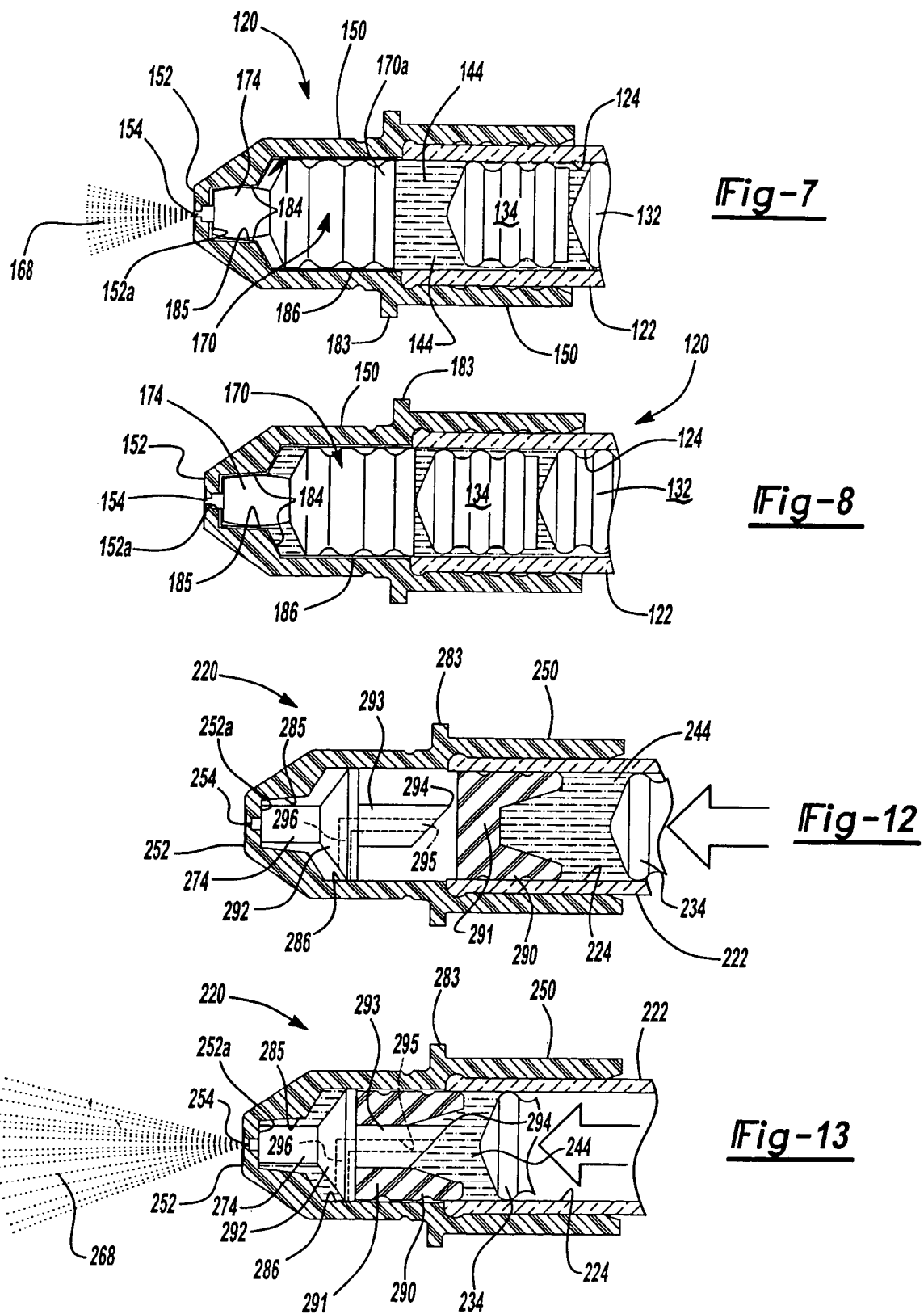

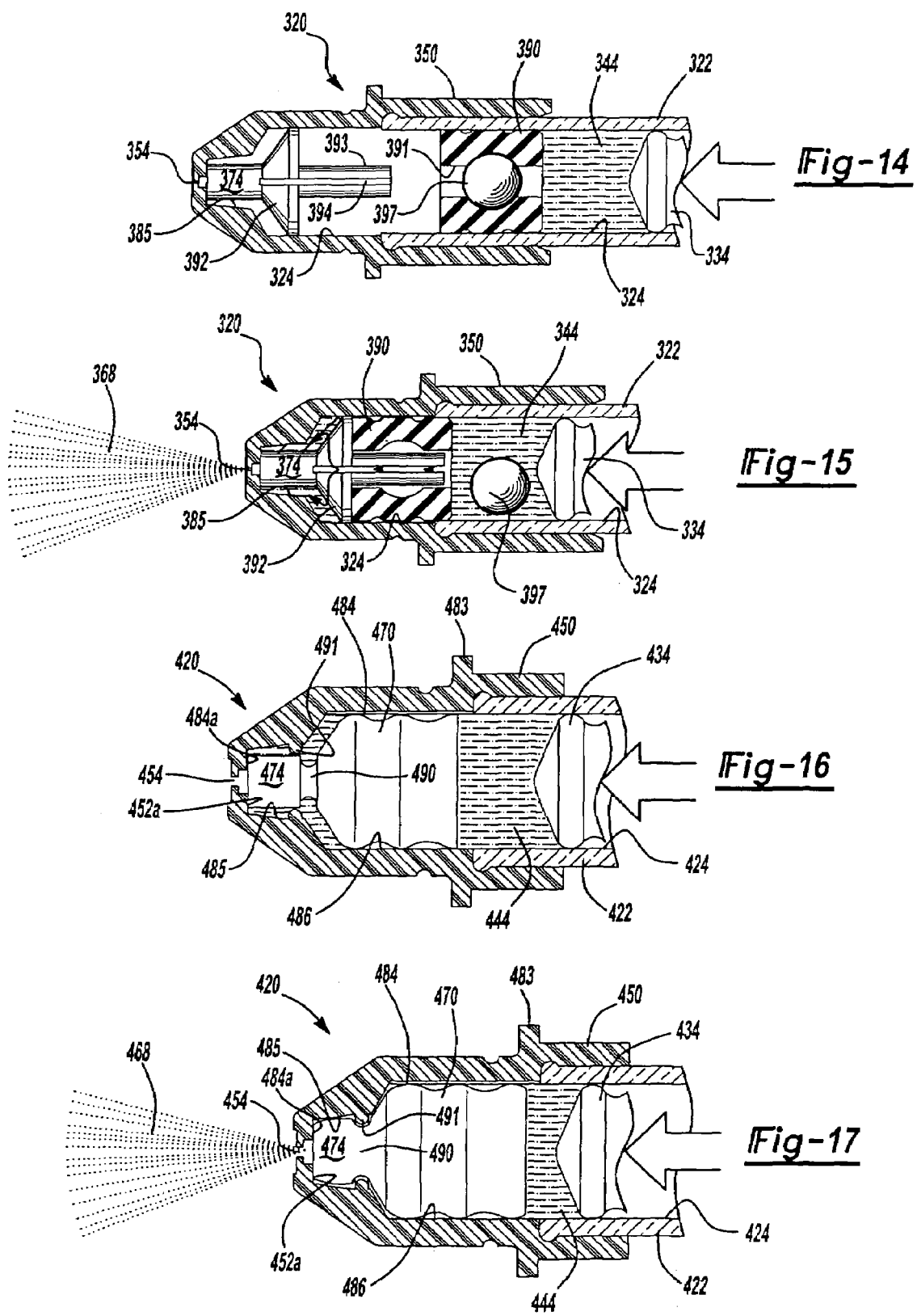

SPRAY DEVICE AND METHOD

FIELD OF THE INVENTION

This invention relates to a spray device which may be utilized to deliver an spray of medicament, drug, vaccine or other substances to a patient for various applications including but not limited to the respiratory system including the mouth or ear of a patient or for topical applications. More specifically, the spray device and method of application of this invention may be utilized to mix a fluid medicament, diluent or solvent or other substance in liquid, powder or lyophilized form and spray the mixture for application to a patient as described.

BACKGROUND OF THE INVENTION

Various spray devices have been developed by the applicant and others which have been in use for many years. As used herein, the terms "substance" or "medical substance" are intended to broadly cover any vaccine, drug, medicament or other substance which, when applied to a patient, results in the cure, alleviation, suspension, prevention, diagnosis or treatment of a disease or condition of the patient. Such spray devices are commonly limited to a liquid medicament which is stored in a container having a spray head and a pump or the container is formed of a flexible polymer and the liquid is forced through the spray head by squeezing the container. Such spray devices are therefore limited to liquid medicaments having a relatively long shelf life. Syringes with a sprayer have also been developed by the applicant as disclosed in U.S. Pat. No. 5,601,077 assigned to the assignee of the present application.

It is also conventional to store medical substances in a sealed vial or other medical container for later use. Such medicaments may be in a dry, lyophilized (freeze-dried) or powder form to increase shelf life. Such dry, lyophilized or powdered drugs are generally stored in a sealed vial and reconstituted in liquid form for administration to a patient by adding a diluent or solvent. There are also liquid medical substances which are particularly efficacious if mixed prior to use, but the mixture has a relatively short shelf life or liquid medical substances which are not stable after mixing. Conventional medical vials for storing medical substances are generally sealed with an elastomeric stopper and a thin malleable metal cap, such as aluminum, encloses the open end of the vial, which is generally crimped beneath the rim of the vial. A dry, lyophilized or powdered medical substance is normally reconstituted by piercing the elastomeric stopper with the needle cannula of a syringe containing the diluent or solvent. Liquid drugs are also mixed prior to use using a hypodermic syringe containing the second liquid substance as described. This method of reconstituting a dry, lyophilized or powder substance or mixing liquid substances therefore requires the use of several steps and manipulation by the patient or healthcare worker including removal of the aluminum cap and the use of a hypodermic syringe having a sharp needle cannula is subject to potential error, contamination or injury. It would therefore be desirable and convenient for a healthcare worker or patient to have a spray device which mixes the liquid and medical substance, preferably at the time of application and which eliminates the requirement for a syringe having a sharp needle cannula.

It is also conventional to mix a liquid and a medical substance in a syringe prior to injection. Such syringes are generally referred to as "two-component syringe assemblies" and include a syringe barrel typically formed of glass having a needle cannula at one end, a bypass spaced from the needle cannula and the open end and a pair of spaced elastomeric stoppers in the syringe barrel spaced from the bypass as disclosed, for example, in U.S. Pat. Nos. 4,599,082 and 5,899,881 both assigned to the assignee of the present application. The chamber in the syringe barrel defined between the stoppers is generally filled with a liquid and the chamber between the second stopper and the needle cannula may contain a liquid, powder or lyophilized substance, whereby movement of the first stopper drives the second stopper to the bypass area and continued movement of the first stopper drives liquid through the bypass, mixing the liquid with the substance in the second chamber. However, this technology has not been applied or adapted for use in a spray device and prior art spray devices are not adapted for mixing fluid or powder substances at the time of application as set forth above. There is, therefore, a need for a spray device, wherein the medical substance may be mixed in the device, preferably at or near the time of the application of the spray to the patient.

SUMMARY OF THE INVENTION

In its broadest application, the spray device of this invention comprises a tubular body or barrel having first and second open ends, a bypass between the open ends, a spray nozzle on the second open end having a spray nozzle port preferably coaxially aligned with the tubular body, first and second spaced stoppers located between the first open end of the tubular body and the bypass, a fluid between the first and second stoppers and a medical substance between the second stopper and the spray nozzle which may be a liquid, powder or lyophilized medical substance. Thus, movement of the first stopper toward the second open end of the tubular body moves the second stopper to the bypass area, causing the fluid to flow between the second stopper and the spray nozzle mixing the fluid with the medical substance. Continued movement of the first stopper drives the first stopper against the second stopper and continued movement of the first stopper drives the mixture of fluid and medical substance through the spray nozzle creating a mist of droplets suitable for application to a patient. As described above, the spray device of this invention may be utilized for various applications including but not limited to delivery to the respiratory system of the patient, topical applications and application of spray to the ear canal. As used herein, the term "respiratory system," broadly covers the nasal and oral passages, lungs, etc.

The preferred embodiments of the spray device of this invention include a third stopper having an external diameter in sealed relation with the internal surface of the tubular body or barrel initially located in the tubular barrel between the second stopper and the second open end of the tubular body, such that movement of the first and second stoppers moves the third stopper into the spray nozzle providing space for mixing of the fluid and substance and expelling air through the spray port. In the most preferred embodiment of the spray device, the spray nozzle includes a body portion having a generally cylindrical internal surface including an internal diameter generally equal to the internal surface of the tubular barrel. The internal surface of the body portion includes a generally longitudinally extending internal passage establishing fluid communication between the tubular barrel and the spray nozzle port when the third stopper is located within the body portion of the spray nozzle. The preferred embodiments of the third stopper of the spray device of this invention further includes a longitudinally extending axial projection having a diameter less than the diameter of the body portion and the spray nozzle includes a central opening configured to receive the longitudinal projection of the third stopper.

In one preferred embodiment, the longitudinal projection of the third stopper is resilient and the overall longitudinal length of the third stopper including the longitudinal projection is greater than the longitudinal length of the body portion of the spray nozzle. In this embodiment, the longitudinal projection of the third stopper is resiliently deformed against an internal surface of the central opening in the spray nozzle, such that the entire body portion of the third stopper is received in the body portion of the spray nozzle, establishing fluid communication between the tubular barrel and the spray nozzle port through the generally longitudinally extending internal groove. In another preferred embodiment, the internal surface of the central opening in the spray nozzle includes an annular rib adjacent the opening which sealingly engages an end portion of the longitudinal projection and the longitudinal projection further includes a reduced diameter neck portion, such that axial deformation of the longitudinal projection receives the annular rib in the reduced diameter neck portion of the longitudinal projection, establishing fluid communication around the longitudinal projection. In this embodiment, it is not necessary for the longitudinal length of the third stopper to be initially greater than the longitudinal length of the spray nozzle.

In the other embodiments of the spray device of this invention, the longitudinal projection of the third stopper is separate from the body portion and may be formed of a nonresilient polymer. In these embodiments, the separate end portion of the third stopper is initially received in the central opening in the spray nozzle and the body portion of the third stopper is initially spaced from the end portion adjacent the second open end of the tubular barrel, such that movement of the first and second stoppers drives the body portion of the third stopper into the body portion of the spray nozzle and against the end portion, establishing fluid communication between the tubular barrel and the spray nozzle port through the generally longitudinally extending internal passage as described above.

Alternatively, the end portion of the third stopper having the longitudinally extending projection may also include means to establish fluid communication through the body portion of the third stopper upon receipt of the body portion of the third stopper in the body portion of the spray nozzle. In one embodiment, the third stopper includes an opening partially through the body portion of the third stopper and a septum sealing the opening, wherein the separate end portion includes an axially projecting piercing element or portion. In this embodiment, movement of the body portion of the third stopper toward the end portion drives the piercing element through the septum, establishing fluid communication through the body portion of the third stopper. In another embodiment, the body portion of the third stopper includes a central passage therethrough and a sealing element, such as a ball in the passage, and the separate end portion includes an axially projecting driver portion configured to be received in the axial passage through the body portion, such that movement of the body portion of the third stopper into the body portion of the nozzle drives the driver portion of the end portion through the axial passage in the body portion of the stopper, removing the sealing element in the passage and establishing fluid communication through the passage.

The method of delivering a fine spray of a medical substance to a patient utilizing the spray device of this invention will now be understood from the description of the device above. In general, the method of delivering a fine spray of medical substance to a patient includes driving the first stopper in the tubular barrel adjacent the first open end of the barrel toward the second stopper until the second stopper reaches the bypass area. The method of this invention then includes continuing to drive the first stopper toward the second stopper, causing the fluid between the first and second stoppers to flow through the bypass and mix the fluid with the medical substance until the first stopper engages the second stopper. Finally, the method of this invention includes driving the first and second stoppers through the tubular barrel, causing the mixture to flow through the spray nozzle, thereby creating a fine mist of the mixture for application to a patient. As set forth above, the method of this invention may be utilized to deliver a fine mist of fluid for various applications including but not limited to delivery to the respiratory system of the patient through the nose or mouth, topical applications and other applications including application of a spray to the ear canal for example.

The method of delivering a fine spray of fluid to a patient utilizing the preferred embodiments of the spray device described above further includes driving or moving the first and second stoppers in the tubular barrel toward the third stopper following mixing as described above. The fluid pressure then drives the third stopper, or the body portion of the third stopper where the end portion and body portion are separate, within the spray nozzle, establishing fluid communication between the tubular barrel and the spray nozzle as described above. Where the longitudinal projection of the third stopper is integral with the body portion, as described above, the method of this invention then includes driving the first and second stoppers toward the third stopper. The fluid pressure then drives the longitudinal projection of the third stopper into the central opening in the spray nozzle, deforming the longitudinal projection axially to establish fluid communication between the tubular barrel and the spray nozzle port as described above.

Alternatively, where the end portion of the third stopper is separate from the body portion and the longitudinal projection of the end portion is initially received in the central opening in the spray nozzle and the body portion is initially spaced from the end portion in the tubular barrel, the method of this invention includes driving the first and second stoppers toward the third stopper, which drives the body portion of the third stopper into the body portion of the spray nozzle into contact with the end portion, establishing fluid communication between the tubular barrel and the spray nozzle port. In one embodiment, wherein the body portion of the third stopper includes a pierceable septum and the separate end portion of the third stopper includes a projecting piercing element or projection, the method of this invention includes piercing the septum in the body portion of the third stopper to establish fluid communication through the body portion of the third stopper. In the other alternative embodiment, wherein the body portion of the third stopper includes an axial passage having a sealing member such as a ball within the axial passage and the separate end portion of the third stopper includes an axially projecting driver portion configured to be received within the passage, the method of this invention includes driving the body portion of the third stopper toward the separate end portion, which drives the axially projecting driver portion through the axial passage in the body portion, establishing fluid communication through the body portion of the third stopper.

The spray device and method of this invention therefore has several advantages over the prior methods of delivering a fine spray of a medical substance to a patient described above. First, the device and method of this invention requires only one container for two substances which, as described above, may comprise a fluid, such as a liquid medical substance, diluent or solvent, or a delivery gas, and the second substance may be a liquid, powder or lyophilized medical substance. Another advantage of the spray apparatus and method of this invention is that the substances can be filled from the opposed open ends of the tubular body or barrel, minimizing the risk of crosscontamination during filling as discussed further below.

The spray device and method of this invention also has safety benefits as described above. First, reconstitution of a dry, powder or lyophilized medical substance or mixing of medical substances does not require use of a syringe or other device having a sharp needle cannula. Further, mixing the fluid and medical substance in the tubular barrel significantly reduced the number of manipulations and steps as compared to the vial and syringe method of reconstituting a medical substance resulting in better aseptic control, reduced error and risk of administration of an incomplete dosage. As will be understood, the tubular body or barrel may be formed of glass or a clear plastic such that the substances are visible before and after reconstitution. Further, as described below, the spray device of this invention may utilize a cap which is received over the spray nozzle, which may be vented by providing discontinuous ribs, permitting movement of the third stopper without removing the cap. Other advantages and meritorious features of this invention will be understood from the following description of the preferred embodiments, the appended claims and the drawings, a brief description of which follows.

BRIEF DESCRIPTION OF THE DRAWINGS

FIG. 1 is a side partially cross-sectioned view of one embodiment of the dual chamber spray device of this invention prior to actuation;

FIG. 2 is a side partially cross-sectioned view of the spray device shown in FIG. 1 following actuation and during mixing of the substances;

FIG. 3 is a side partially cross-sectioned view of the spray device shown in FIGS. 1 and 2 near completion of the spray sequence;

FIG. 4 is a side partially cross-sectioned view of a preferred alternative embodiment of the spray device of this invention prior to actuation;

FIG. 5 is a side partially cross-sectioned view of the spray device shown in FIG. 4 during actuation and mixing of the substances;

FIG. 6 is a side partially cross-sectioned view of the spray device in FIGS. 4 and 5 following mixing of the substances;

FIG. 7 is a partial side view partially cross-sectioned of the spray device in FIGS. 4 to 6 during spraying;

FIG. 8 is a partial side partially cross-sectioned view of the spray device similar to FIG. 7 following completion of the spray;

FIG. 12 is a partial side partially cross-sectioned view of an alternative embodiment of the spray device of this invention during actuation;

FIG. 13 is a partial side partially cross-sectioned view of the embodiment of the spray device shown in FIG. 12 near completion of the spray sequence;

FIG. 14 is a partial side partially cross-sectioned view of a further alternative embodiment of the spray device of this invention during actuation;

FIG. 15 is a partial side partially cross-sectioned view of the spray device shown in FIG. 14 near completion of the spray sequence;

FIG. 16 is a partial side partially cross-sectioned view of a further alternative embodiment of the spray device of this invention during actuation; and FIG. 17 is a partial side partially cross-sectioned view of the spray device shown in FIG. 16 near completion of the spray sequence.

DETAILED DESCRIPTION OF THE PREFERRED EMBODIMENTS

Figure 9:
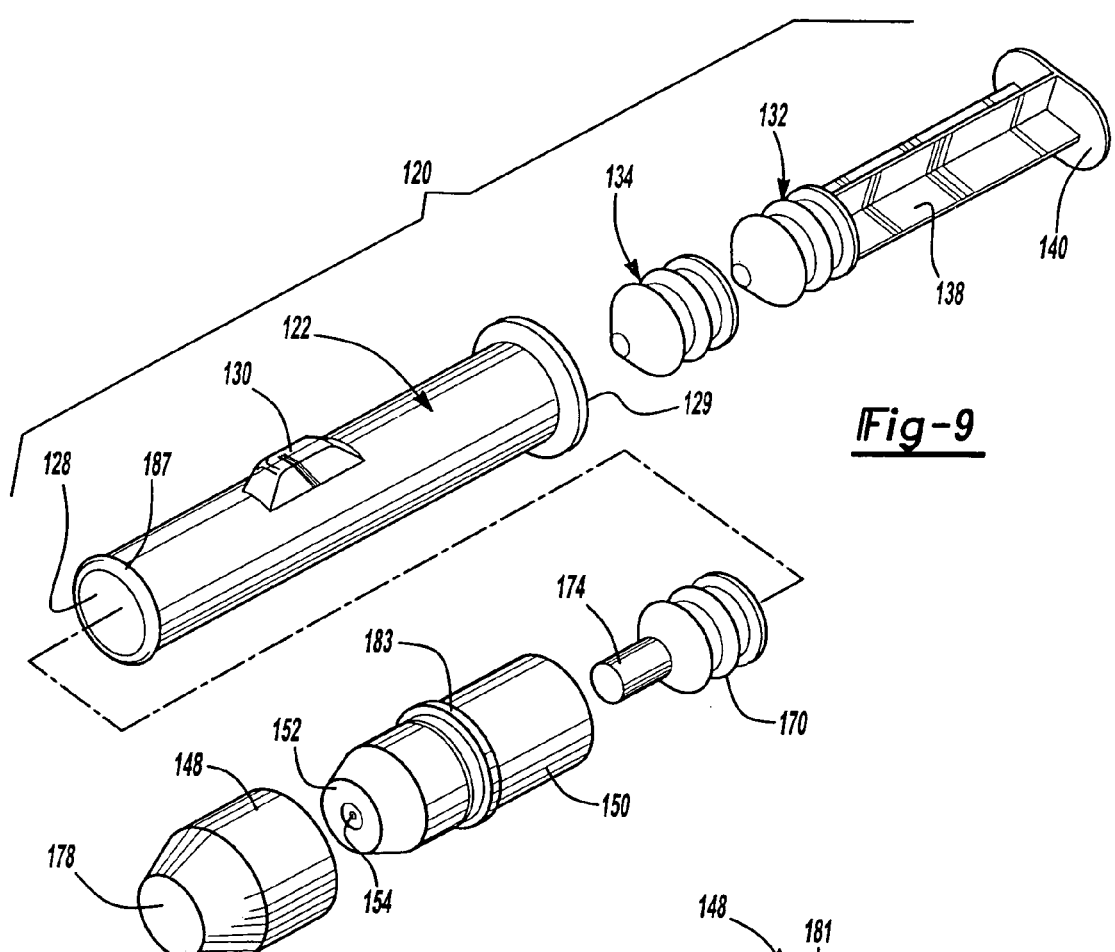
FIG. 9 is an exploded perspective view of the components of the spray device shown in FIGS. 4 to 8.

As set forth above, the spray device of this invention combines the advantages of a dual chamber or two-component syringe in a spray device for various spray applications of a medical substance, which eliminates the requirement of mixing the constituents of the substances using a hypodermic syringe or cartridge having a sharp needle cannula and a vial having an elastomeric stopper and malleable metal cap. The embodiments of the spray device of this invention illustrated in the drawings and described below provides mixing of substances in the body of the spray device and spray of a fine mist of medical substances for various applications including, but not limited to, the respiratory system of the patient through the nose or mouth, topical applications and other applications including, for example, applications through the patient's ear canal.

In the embodiment shown in FIGS. 1 to 3, the spray device 20 includes a tubular body or barrel 22 having a generally cylindrical internal surface 24, a reduced diameter tip portion 26 having a distal open end 28 and a proximal open end 29. For the purposes of description only, the "proximal end" refers to the end of the device closest to the hand of the patient or healthcare worker holding the spray device and the "distal end" refers to the end furthest from the person holding the spray device. The tubular body or barrel 22 further includes a bypass 30 in the form of a longitudinally enlarged portion or bulge having a channel 31 permitting passage of fluid through the bypass 30 as described below. As stated below, the bypass 30 may have alternative forms including internal ribs, etc.

The spray device 20 further includes a first stopper 32 adjacent the proximal open end 29 of the tubular body 22 and a second stopper 34 spaced from the first stopper 32 and located between the proximal open end 29 and the bypass 30. In the disclosed embodiment, the second stopper 34 is located in the tubular body 22 adjacent the bypass 30. The stoppers 32 and 34 may be conventionally formed of a resilient or elastomeric material, such as rubber, synthetic rubber, plastic, etc., and preferably include a plurality of spaced annular ribs 36 which sealingly engage the internal cylindrical surface 24 of the tubular barrel 22 as shown, but the stoppers 32 and 34 are moveable within the tubular barrel 22 as will be understood by those skilled in this art. In the disclosed embodiment, the proximal or first stopper 32 includes a conventional plunger 38 having a proximal flange portion 40, such that the user of the spray device 20 can drive the first stopper 32 toward the distal or second stopper 34 as described further below. The plunger 38 may be cruciform in shape as shown and may be formed integral with the stopper 32, the end portion 38 may be threaded into the first stopper 32 (not shown) or otherwise secured as is conventional with hypodermic syringes. Alternatively, the spray device may be in the form of a cartridge, wherein the plunger 38 is replaced by a drive means (not shown) which drives the first stopper 32 toward the second stopper 34 as is conventional with medical cartridges. The first and second stoppers 32 and 34 respectively divide the tubular body 22 into a first chamber 42, between the first and second stoppers, and a second chamber 44 between the second stopper 34 and the distal open end 28 of the tubular barrel. As described below, the first chamber 42 is filled or partially filled with a fluid, such as a liquid or a gas and the second chamber 44 is at least partially filled with a liquid, powder or lyophilized medical substance which are mixed in the spray device 20 during actuation of the device.

The spray nozzle and cap assembly 46 may be conventional for spray devices of this type, such as the spray nozzle and cap assembly disclosed in the above-referenced U.S. Pat. No. 5,601,077 assigned to the assignee of the present invention. The spray nozzle and cap assembly 46 disclosed in FIGS. 1 to 3 includes a cup-shaped cap 48, a tubular nozzle body 50 having a distal end portion 52 and a spray nozzle port 54 preferably coaxially aligned with the longitudinal axis of the cylindrical internal surface 24 of the tubular barrel 22. The spray nozzle and cap assembly further includes a valve 56 located between the distal open end 28 and the end portion 52 of the tubular nozzle body 50. As described more fully in the above-referenced U.S. Pat. No. 5,601,077, the valve 56 includes a cylindrical portion 58 coaxially aligned with the spray nozzle port 54 and an annular skirt portion 60. The disclosed embodiment of the spray nozzle prevents unpressurized fluid in the tubular barrel 22 from flowing through the spray nozzle port 54 while allowing fluid under pressure to flow distally through the spray nozzle port 54. The tubular nozzle body 50 in the disclosed embodiment is retained on the tip portion 26 of the tubular barrel 22 by an interference fit, but may be attached by any suitable means including but not limited to threading, thermal welding, gluing, etc.

The operation of the two-chamber spray device 20 shown in FIGS. 1 to 3 may now be described, as follows. First, the tubular barrel is at least partially filled with a substance suitable for mixing prior to application. The first chamber 42 between the first and second stoppers 32 and 34, respectively, is filled with a fluid, which may be a fluid medical substance, liquid solvent or diluent for the substance in the second chamber 44 or a delivery gas. Thus, the second chamber 44 may be partially filled with a liquid or a powdered or lyophilized medical substance as described above. The fluid in the first chamber 42 is then mixed with the substance in the second chamber 44 by driving the first stopper 32 toward the second stopper 34 or toward the distal open end 28 of the tubular barrel 22. In the disclosed embodiment, this is accomplished by driving the plunger 38 into the tubular barrel 22 as shown by arrow 62 in FIG. 2. The fluid in the first chamber 42 thus drives the second stopper 34 into the barrel opposite or facing the bypass 30 as shown in FIG. 2, wherein the fluid in the first chamber 42 is driven through the passage 31 in the bypass 30 as shown by arrow 64 in FIG. 2, wherein the fluid in the chamber 42 is mixed with the substance in the second chamber 44. The cap 48 may be removed prior to actuation of the spray device 20 as shown in FIG. 2 or the cap may include air passages as described below in regard to FIG. 11. The first stopper 32 then engages the second stopper 34 driving the mixture in the second chamber through the second or distal open end 28 of the tubular barrel or body 22 as shown by arrows 66 in FIG. 3 forming a fine spray or mist of droplets 68 as shown in FIG. 3. During actuation of the spray device 20, the mixed fluid received in the tubular nozzle body 50 under pressure through the distal open end 28 of the tubular barrel deforms the annular skirt portion 60 which is formed of a resilient material such as natural or synthetic rubber, or plastic, permitting the fluid to flow through the nozzle body 50 to the spray nozzle port 54, generating the fine spray 68.

A preferred embodiment of the spray device 120 shown in FIGS. 4 to 11 will now be described. The spray device 120 includes a tubular body or barrel 122 having a generally cylindrical internal surface 124, a distal open end 128 and a proximal open end 129. In this embodiment of the spray device 120, the proximal open end 129 of the tubular body 122 has a cylindrical internal surface 124 having the same diameter as the distal open end 128. For ease of description, like elements of the spray device 120 is numbered in the same sequence as the spray device 20 shown in FIGS. 1 to 3. The tubular body or barrel 122 also includes a bypass 130 having a passage or channel 131 as described above in regard to the spray device 20 shown in FIGS. 1 to 3.

The spray device further includes a proximal or first stopper 132 adjacent the proximal open end 129 and a second stopper 134 spaced from the first stopper 132 and located in the tubular barrel 122 between the first stopper 132 and the bypass 130. As described above in regard to FIGS. 1 to 3, the stoppers 132 and 134 may be formed of a resilient material, such as natural or synthetic rubber, plastic, etc., and preferably includes a plurality of spaced annular ribs 136 which sealingly engage the cylindrical internal surface 124 of the tubular barrel 122. The first stopper 132 may include a plunger 138 fixed to or integrally formed with the first stopper 132. Alternatively, the plunger 138 may be replaced with a conventional drive means such as conventionally used with medical cartridge as described above. The plunger may be cruciform in cross-section and may include a flange 140 for driving the first plunger through the tubular barrel 122.

In the preferred embodiment of the spray device 120 shown in FIGS. 4 to 11 and the remaining figures, the spray device includes a third stopper 170 located between the bypass 130 and the open distal end 128 of the tubular barrel 122. The third stopper 170 is preferably located generally adjacent the open distal end 128 of the tubular barrel 122 and initially located within the tubular barrel 122. The third stopper 170 may also be formed of a resilient plastic or elastomeric material, and in the disclosed embodiment includes a plurality of spaced annular ribs 172 which sealingly engage the internal surface 124 of the tubular barrel 122 as shown. The most preferred embodiments of the third stopper 170 shown in FIGS. 4 to 11 and the embodiments described in the remaining figures include a longitudinal projection or stalk 174 preferably having a diameter substantially less than the diameter of the body portion of the third stopper 170 as shown. A first chamber 142 is thus defined in the tubular barrel 122 between the first and second stoppers 132 and 134 and a second chamber 144 is defined between the second stopper 134 and the third stopper 170 as shown in FIG. 4. The first chamber 142 is at least partially filled with a fluid, such as a liquid medical substance, diluent, solvent, or a delivery gas, and the second chamber 144 may be partially filled with a substance, such as a liquid, or a powder or lyophilized medical substance. The proportions of the chambers 142 and 144 will depend on the substances in the chambers and the particular application.

Figure 10:
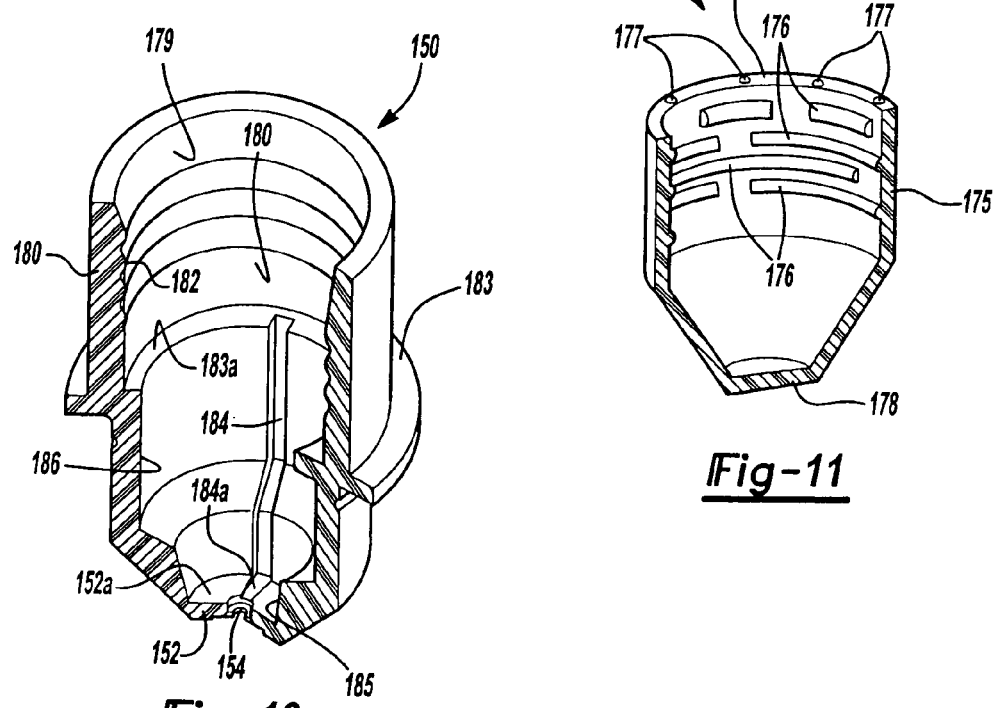
FIG. 10 is a side cross-sectioned perspective view of the spray nozzle in the spray device shown in FIGS. 4 to 9.
Figure 11:
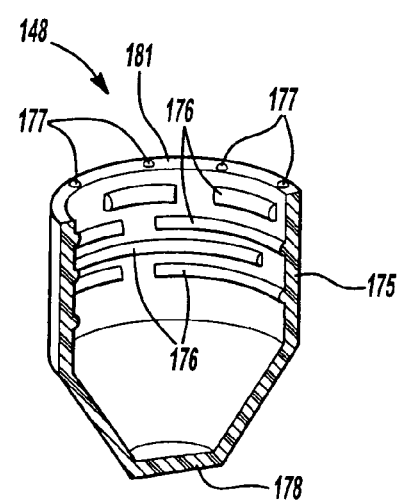
FIG. 11 is a side cross-sectioned perspective view of one embodiment of the end cap in the spray device shown in FIGS. 4, 5 and 9.

The spray nozzle and cap assembly 146 includes a cup-shaped cap 148 described further below in regard to FIG. 11 and a spray nozzle body 150 described further below in regard to FIG. 10. As best shown in FIG. 11, the cup-shaped cap 148 includes a tubular portion 175 including a plurality of spaced discontinuous internal annular ribs 176 extending transverse to the longitudinal axis of the cap 148 and an enclosed end portion 178. The end surface 181 may also include a plurality of spaced protuberances 177 at the open end to assure purging of air from the cap as described below. The spray nozzle 150 best shown in FIG. 10 includes a tubular body portion 180, open end 179, an internal surface including a plurality of internal ribs 182, a radial flange portion 183 and at least one longitudinal groove or passage 184 extending from the internal flange portion 183a to the closed end 152 having a spray nozzle port 154 which may be coincident with the longitudinal axis of the tubular body portion 180 and the longitudinal axis of the tubular barrel 122 as shown. The generally longitudinal passage 184 further includes a generally radial component (with respect to the longitudinal axis) 184a to the spray port 154. Alternatively, the passages 184 and 184a may be replaced with ribs. The spray nozzle further includes a central recess or opening 185 configured to receive the longitudinal projection or cylindrical stalk 174 of the third stopper 170. It should also be noted that the diameter of the internal surface 180 of the spray nozzle 150 in this embodiment is preferably equal to the internal diameter of the cylindrical internal surface 124 of the tubular barrel 122 and coaxially aligned therewith as best shown in FIGS. 4 to 6. Alternatively, as discussed below, the internal diameter of the internal surface 180 may be greater than the internal diameter of the barrel, such that the internal "passage" surrounds the stopper 134.

FIG. 9 illustrates the assembly of the spray device 120 illustrated in FIGS. 4 to 6. One advantage of the tubular barrel 122 including an open distal end 128 having the same internal diameter as the cylindrical internal surface 124 (see FIGS. 4 to 6) is that the fluid and substance in the chambers 142 and 144 may be loaded from opposite ends of the tubular barrel, thereby minimizing the risk of crosscontamination of the medical substance and fluid. Thus, the second stopper 134 is first assembled in the tubular barrel 122 adjacent to the bypass 130 as shown in FIG. 4. The fluid may then be received in the chamber 142 (see FIGS. 4 to 6) and the first stopper is then inserted into the open proximal end 129 as best shown in FIG. 4. The substance may then be received in the open distal end 128 and the third stopper 170 is then received in the open distal end 128 forming the second chamber 144. As set forth above, the substance in the second chamber 144 may include a liquid, a powder or a lyophilized substance. The distal end of the tubular barrel 122 includes an external rib 187 as shown in FIGS. 4 to 6 and 9 which receives the internal ribs 182 of the spray nozzle 150 as shown in FIGS. 4 to 6 until the internal flange portion 183a engages the distal end of the tubular barrel. Alternatively, the ribs 182 may be replaced with an internal thread or the parts may be otherwise secured. The cup-shaped cap 148 may then be received over the distal end 152 of the spray nozzle or preassembled on the spray nozzle as shown in FIGS. 4 to 6. The embodiment of the spray device 120 is then ready for activation and use.

Having described the components of the embodiment of the spray device 120 shown in FIGS. 4 to 11 and its assembly, it is now possible to describe the operation of the spray device during use. First, the first stopper 132 is driven toward the second stopper 134 such as by operation of the plunger 138 as described above in regard to the spray device 20 shown in FIGS. 1 to 3. This movement of the first stopper 132 toward the second stopper 134 as shown by arrow 162 in FIG. 5 drives the fluid in the first chamber 142 against the second stopper 134, which drives the second stopper into the barrel opposite the bypass 130 as shown in FIG. 5, wherein the fluid in the first chamber 142 flows through the channel 131 in the bypass to mix with the substance in the second chamber 144 as shown by arrow 164. As the second chamber 144 fills with fluid, the third stopper 170 moves toward the nozzle body 150 providing space for the mixture and assuring complete mixing, which is a unique feature of the spray device 120 of this invention and the embodiments shown in the remaining figures as described below. During movement of the third stopper 170 into the nozzle body 150, air entrapped between the third stopper and the nozzle 150 escapes through the longitudinal passage 184 and is purged from the nozzle through the discontinuous ribs 176 shown in FIG. 11 as shown by arrows 188 in FIG. 5. The cap 148 is then removed and the spray device is ready for spray application to a patient. Alternatively, the cap 148 may be removed prior to actuation of the spray device particularly where the cap does not include venting means.

As will be understood from the description above of the operation of the spray device 20 shown in FIGS. 1 to 3, mixing of the fluid in chamber 142 with the substance in the chamber 144 is complete when the first stopper 132 engages the second stopper 134 as shown in FIG. 6. The spacing between the second stopper 134 and the third stopper 170 will depend upon the volume of the substance in the second chamber 144 where the substance is a liquid or gas. Alternatively, where the substance in the second chamber 144 is a dry or lyophilized powder, the spacing will be adjusted dependent upon the volume of powder and the spacing necessary for thorough mixing. As the volume of fluid in chamber 144 increases, the third stopper 170 is moved toward the nozzle 150 (which is to the left in the Figures), the air between the third stopper 170 and the spray port 154 is purged around the discontinuous ribs 176 and the protuberances 177 best shown in FIG. 11 until the cylindrical projection 174 is fully received in the configured opening 185 as shown in FIG. 6. In the most preferred embodiment, to prevent the mixture in the second chamber 144 from flowing through the spray nozzle port 154 until mixing is complete, the longitudinal length "L" of the third stopper 170 including the body portion and the cylindrical stalk 174 is slightly greater than the longitudinal length of the internal surface of the nozzle body 150 measured from the interior surface 152a of the end portion 152 of the nozzle to the abutment surface 183a of the radial flange 183 which engages the distal end 128 of the tubular barrel as shown in FIG. 10. Thus, the mixture in the second chamber 144 is prevented from flowing from the spray nozzle port 154 until the body portion of the third stopper 170 is moved fully into the spray nozzle.

Finally, after complete mixing of the fluid and substance in the second chamber 144 and driving of the first stopper 132 against the second stopper 134 as shown in FIG. 6, the stalk portion 174 of the third stopper 170 is driven against the opposed surface 152a of the end portion 152 which also defines the end wall of the central recess 185. Compression of the stalk portion 174 against the face 152a deforms the stalk 174 as shown in FIG. 7, such that the body portion of the third stopper 170 is fully received in the cylindrical passage 186 in the nozzle 150 as shown in FIG. 7, wherein the fluid in the second chamber 144 is in fluid communication with the spray nozzle port 154 through generally longitudinal passages 184 and 184*a* shown in FIG. 10 which continues through the surface 152*a* as shown. The mixture in chamber 144 then flows under pressure through the longitudinal channel 184 and 184*a* to the nozzle port 154, generating a fine spray or mist of fluid 168 as shown in FIG. 7. As set forth above, the third stopper 170 including the integral stalk portion 174 is preferably formed of a resilient or deformable material, such as natural or synthetic rubber, but may also be formed of a resilient polymer. Alternatively, the stalk portion 174 may be formed of a resilient material different from the body portion of the third stopper 170 or the end of the third stopper 170 including the stalk portion 174 may be separate from the body portion as described below in regard to the embodiments of the spray device disclosed in FIGS. 12 to 15. Finally, when the second stopper 134 engages the third stopper 170 as shown in FIG. 8, the second chamber 144 shown in FIG. 7 is virtually empty. As will be understood by those skilled in this art, the spray devices of this invention may be utilized for a single dose application or multiple doses, wherein the tubular barrel 122 may be marked with suitable indicia for each dose and the tubular barrel is preferably formed of glass or clear plastic to permit visualization of the mixing of the fluid and substance and volume of the mixture remaining in the second chamber 144.

FIGS. 12 to 14 illustrate further embodiments of the spray device of this invention wherein the third stopper is comprised of two separate components which provide fluid communication through the third stopper. In the embodiment of the spray device 220 shown in FIGS. 12 and 13, the tubular barrel 222 and the first and second stoppers may be identical to the spray device 120 disclosed in FIGS. 4 to 11 described above. Only the leading portion of the second stopper 234 is shown in FIGS. 12 and 13 as required for a full description of this embodiment. The spray nozzle 250 may be identical to the spray nozzle 150 described above, except that the longitudinal channel 184 is not required or necessary, but the transverse channel 184*a* in surface 152*a* is required unless the end of the stalk 174 includes a radial groove. No further description of the spray nozzle 250 is therefore required and the elements of the spray nozzle are numbered in the same sequence as the spray nozzle 150 described above. In this embodiment of the spray device 220, the third stopper is comprised of a body portion 290 which sealingly engages the internal surface 224 of the tubular barrel 222 having a reduced thickness axial portion or septum 291 and an end part 292 which includes the cylindrical axial projection or stalk 274. The end part 292 is preferably formed of a hard plastic and the projecting axial stalk portion 274 may be initially received in the central axial opening 285 as shown. The end part 292 further includes an axially projecting piercing element 293 which may be integral with the end part 292 having a sharp end 294 extending opposite the stalk portion 274 toward the septum 291 of the body portion 290 as shown in FIG. 12. The piercing element 293 may be cylindrical and includes an axial passage 295 which communicates with the radial passage 296 in the end part 292 as shown in FIGS. 12 and 13. The interior surface 252*a* of the end portion 252 of the nozzle member 250 may include a radial groove shown in surface 152*a* in FIG. 10 or the end of the stalk 274 may include a radial groove to provide fluid communication to the spray nozzle port 254.

The actuation of the spray device 220 shown in FIGS. 12 and 13 may then be described, as follows. As described above, the initial actuation of the spray device 220 is identical to the spray device 120 described above, wherein the first stopper (not shown) is driven toward the second stopper 234 to mix the fluid and substance in the second chamber 244. Movement of the second stopper 234 then drives the body portion 290 of the second stopper assembly into the cylindrical internal surface 286 of the nozzle member drives the sharp end 294 of the piercing element 293 through the reduced thickness axial portion or septum 291 of the body portion 290 to pierce the septum 291 as shown in FIG. 13 and establishing communication through the axial and radial passages 295 and 296, respectively to the spray nozzle port 254, resulting in a fine spray or mist 268 as shown in FIG. 13. As will be understood, the fluid and substance in the chamber 244 will be thoroughly mixed and pressurized by the second stopper 234 prior to piercing of the septum 291 to establish a spray 268 as described above in regard to the embodiment of the spray device 120.

The actuation and operation of the spray device 320 shown in FIGS. 14 and 15 is similar to the operation of the spray device 220 shown in FIGS. 12 and 13 in that the third stopper is comprised of two separate components which cooperate to establish communication through the stopper assembly. In the embodiment of the spray device 320 shown in FIGS. 14 and 15, the third stopper assembly is comprised of a body portion 390 and a separate end part 392 having an integral stalk portion 374 which may be initially received in the central opening 385 of the nozzle member 350 as shown. The nozzle member 350 may be identical to the nozzle member 250 described above in regard to FIGS. 12 and 13 and has been numbered in the same sequence. Therefore no further description of the nozzle member 350 is required. In this embodiment, the body portion 390 of the third stopper includes an axial passage 391 sealed with a ball 397 or other suitable removable sealing element. As described above, the body portion 390 of the third stopper is preferably formed of a resilient material, such as natural or synthetic rubber or resilient plastic, and the ball 397 may be hollow and formed of a suitable polymer, metal, glass or the like. The end part 392 of the third stopper assembly includes an axially projecting stalk portion which may be initially received in the central opening 385 of the nozzle member 350 and the body portion 390 is initially spaced from the end part 392 in sealed relation with the cylindrical internal surface 324 of the tubular barrel 322 as described above in regard to FIGS. 12 and 13. The end part 392 further includes a bifurcated driver element or portion 393 extending axially opposite the cylindrical projection 374 configured to be received in the axially passage 391 in the body portion 390. The slot or space 394 between the bifurcated driver portions 393 extends through the end part 292 as shown in FIG. 14, such that fluid communication is provided through the end part 392 as shown. Alternatively, end part 392 could be tubular or solid and the conical portion could include a passage.

The actuation of the spray device 320 shown in FIGS. 14 and 15 is similar to the embodiment of the spray device 220 described above with reference to FIGS. 12 and 13. As described above, the spray device 320 includes a tubular barrel 322 having a bypass as shown in FIGS. 4 to 6 (not shown in FIGS. 14 and 15) and a first and second stopper spaced as described above. FIGS. 14 and 15 illustrate only the second stopper 334. During actuation, the first stopper (not shown) is driven toward the second stopper 334, and the fluid in the first chamber drives the second stopper 334 into the barrel adjacent the bypass (not shown), driving the fluid in the first chamber into the second chamber 344. Continued movement of the first stopper against the second stopper 334 drives the body portion 390 of the third stopper assembly into the cylindrical internal surface 324 of the nozzle member, which drives the driver portion 393 of the end part 392 into the passage 391 of the body portion 390. The driver portion 393 then drives the ball 397 out of the passage 391 as shown in FIG. 15, establishing fluid communication between the second chamber 344 and the spray nozzle port 354 through the passage 394, generating a spray 368 as described above.

The actuation of the embodiment of the spray device 420 shown in FIGS. 16 and 17 is similar to the embodiment of the spray device 120 shown in FIGS. 4 to 11 described above. In this embodiment, the third stopper 470 includes an integral axial projection or stalk portion 474 similar to the third stopper 170 described above, except that the stalk portion 474 further includes a reduced diameter neck portion 490 as shown in FIG. 16. The nozzle member 450 may be identical to the nozzle member 150 described above, except that the central opening 485 includes an annular rib 491 adjacent the opening to the central opening 485 as shown in FIG. 16. It should also be noted that the inner wall of the central opening 485 is preferably slightly conical as shown in FIG. 16. The remainder of the spray device 420 shown in FIGS. 16 and 17 may be identical to the embodiments described above. That is, the spray device includes a tubular barrel 422 having opposed open ends, first and second spaced stoppers located within the tubular barrel as described above. Further, the cylindrical surface 486 of the nozzle member 450 includes a generally longitudinally extending groove or slot 484, such as shown at 184 in FIG. 10 having a transverse groove 484a in the surface 452a as described above. The actuation of the spray device 420 may now be described as follows.

The third stopper 470 may be initially spaced from the nozzle member 450 as described above in regard to the embodiment of the spray device 120 shown in FIGS. 4 to 11. Alternatively, the stalk portion 474 may be initially received in the conical central opening 485 as shown in FIG. 16. When the stalk portion 474 is received in the central opening 485, the annular rib 491 seals against the external surface of the stalk portion 474 as shown in FIG. 16. Then, following mixing of the substance and fluid in second chamber 444 and driving of the second stopper 434 toward the third stopper, the stalk portion 474 is deformed axially against the internal surface 452a of the end portion 452 as shown in FIG. 17, which reduces the axial length of the stalk portion and receives the annular rib 491 in the reduced diameter neck portion 490 as shown in FIG. 17. Receipt of the annular rib 491 in the reduced diameter neck portion 490 establishes fluid communication through the generally axially extending groove shown at 484 and the groove 484a in the transverse surface (also shown at 152a in FIG. 10) providing fluid communication between the second chamber 444 and the spray nozzle port 454 as shown in FIG. 17, driving the fluid through the spray nozzle port 454 and providing a fine mist 468 through the nozzle as described above.

Having described several embodiments of the spray device of this invention, it will be understood that various modifications may be made to such embodiments within the purview of the appended claims. Where the first chamber 42, 142, etc. includes a liquid, the second chamber 44, 144, etc. may include a second liquid, powder or lyophilized medicament for example. Alternatively, the first chamber may include a carrier gas, such as compressed air for example, and the second chamber may include a powder or lyophilized medicament, such that the spray device of this invention may be used to deliver a spray of powder or lyophilized medicament to the respiratory system of a patient through the nose or mouth. Although a gas is compressible, sufficient pressure may be generated in the first chamber by the first stopper to deliver the gas through the bypass to aerosolize the powder for delivery to a patient. For example, various spray nozzles may be utilized with the dual chamber spray device of this invention. In the preferred embodiments, the tubular barrel has a substantially constant diameter to permit filling or loading of the spray device from the opposed ends to avoid crosscontamination of the fluid and substance as described above. As set forth above, the terms "substance" and "medical substance" are intended to broadly cover any drug, vaccine or medicament which may be applied in the form of a spray to a patient. The cap 148 having spaced internal ribs 176 as shown in FIG. 11 may be utilized with any of the disclosed embodiments of the spray device of this invention including FIGS. 1 to 3 to permit purging of air between the third stopper and the spray nozzle port as described above. Alternatively, the cap may be a conventional cup-shaped cap, wherein the cap is removed prior to actuation. The bypass 30, 130, etc. may also take various forms other than the outwardly bulging semicircular passage shown. For example, the bypass may comprise a plurality of outwardly bulging semicircular passages or the bypass may comprise one or a plurality of inwardly projecting ribs which engage the resilient second stopper providing an internal passage or passages permitting the flow of fluid past the second stopper when the second stopper is located opposite the inwardly projecting portions of the barrel.

Further, in the preferred embodiments of the spray device, wherein the nozzle member includes a generally longitudinally extending internal groove 184, 184a, the internal diameter 186 is preferably generally equal to the internal diameter 124 of the barrel as shown. However, the internal diameter of the spray nozzle may be substantially greater than the internal diameter of the barrel, eliminating the requirement for the longitudinal portion 184 of the internal passage, wherein the mixed fluid and substance flows around the third stopper when the third stopper is located within the nozzle body. In this embodiment, the projecting stalk portion 174 is received in the central opening 185 during actuation of the spray device and, upon axial deformation of the stalk portion, the body portion of the third stopper is received within the larger diameter internal surface of the spray nozzle, permitting the mixed fluid and substance to flow around the body portion of the third stopper into the spray nozzle port through the passage 184a as described above. As used herein, the term "generally longitudinal passage" would then include the annular passage around the body portion of the third stopper. Alternatively, the tubular barrel of the spray device may include a longitudinal groove or rib on the inside surface extending from the distal end and providing fluid communication to the nozzle port. In this embodiment, the third stopper does not have to be received within the body of the nozzle and the nozzle may be secured to the end of the barrel. The longitudinal groove would preferably have a length generally equal to the body portion of the third stopper for the reasons stated above. Where a removable sealing member is provided in a passage through the third stopper 390 as shown at 397 in FIGS. 14 and 15, the removable sealing member 397 may take any shape and maybe captured in an opening in the second stopper to reduce the dead volume of the mixture upon completion of the spray sequence. The embodiments of the spray device disclosed herein provide for thorough mixing of a fluid, such as liquid medical substance, diluent or solvent and a liquid, lyophilized or powder medical substance without the requirement of a hypodermic syringe having a sharp needle cannula and a vial having a pierceable stopper and an aluminum cap as set forth above. The tubular barrel may be formed of glass or a clear polymer, permitting visualization of the mixing of the fluid and substance and to provide for one or multiple doses as described. The invention is now claimed, as follows.

The invention claimed is:

1. A spray device, comprising:
   a tubular barrel having an internal surface,
   opposed first and second open ends and a bypass between said first and second open ends,
   a spray nozzle member on said second open end of said tubular barrel including an internal surface and a spray port, first, second and third stoppers located within said tubular barrel each having an external surface engaging said internal surface of said tubular barrel and moveable in said tubular barrel, said first stopper initially located adjacent said first open end of said tubular barrel, said second stopper spaced from said first stopper and initially located between said first stopper and said bypass of said tubular barrel and said third stopper having a body portion located between said bypass and said second open end of said tubular barrel, a fluid located between said first and second stoppers and a substance located between said second and third stoppers,
   wherein said third stopper includes a longitudinal projection and said spray nozzle includes a recess coaxially aligned with said spray port configured to receive said longitudinal projection,
   whereby movement of said first stopper toward said second open end of said tubular barrel moves said second stopper to adjacent said bypass causing said fluid to flow between said first and second stoppers through said bypass, mixing said fluid between said first and second stoppers with said substance between said second and third stoppers, continued movement of said first stopper then drives said first stopper against said second stopper and continued movement of said first and second stoppers drives said third stopper toward said spray nozzle member said longitudinal projection is deformable against an internal surface of said recess, whereby movement of said third stopper receives said longitudinal projection in said recess in said spray nozzle member and continued movement of said third stopper axially compresses said longitudinal projection providing fluid communication between said tubular barrel and said spray port through an internal passage creating a spray of said mixture for delivery of said mixture to a patient.

2. The spray device as defined in claim 1, wherein said internal surface of said spray nozzle member includes a generally longitudinal internal passage providing fluid communication between said tubular barrel and said spray port of said spray nozzle member only when said third stopper is located in said spray nozzle member.

3. The spray device as defined in claim 1, wherein said third stopper has a longitudinal length greater than the longitudinal length of said internal surface of said spray nozzle member and said longitudinal projection is compressible, whereby compression of said longitudinal projection drives said third stopper within said spray nozzle member providing fluid communication between said tubular barrel and said spray port through said internal passage.

4. The spray device as defined in claim 1 wherein said longitudinal projection is deformable and includes a reduced diameter neck portion and said recess includes a radially projecting annular rib adjacent an open end of said recess, whereby movement of said third stopper deforms said longitudinal projection, receiving said internal radial rib into said reduced diameter neck portion establishing fluid communication between said tubular barrel and said spray port of said spray nozzle member.

5. The spray device as defined in claim 2, wherein said body portion of said third stopper includes an external surface engaging said internal surface of said tubular barrel and a separate end portion including a projecting portion having a diameter less than said body portion of said third stopper received in an opening of said spray nozzle coaxially aligned with said spray port configured to receive said projecting portion, wherein said body portion of said third stopper is initially spaced from said end portion, whereby movement of said body portion of said third stopper into engagement with said end portion receives said body portion in said spray nozzle member establishing fluid communication between said tubular barrel and said spray port through an internal passage.

6. The spray device as defined in claim 5, wherein said body portion of said third stopper includes a passage therethrough and a movable sealing element in said passage, and said end portion of said third stopper includes a projecting driver portion configured to be received in said passage, whereby movement of said body portion of said third stopper toward said end portion drives said driver portion through said passage, moving said removable sealing member and providing fluid communication through said passage.

7. The spray device as defined in claim 5, wherein said body portion of said third stopper includes a pierceable septum and said end portion includes a projecting piercing element projecting toward said septum, whereby movement of said body portion of said third stopper toward said end portion drives said projecting piercing element through said septum providing fluid communication through said body portion with said spray port.

* * * * *